United States Patent [19]

Ichikawa et al.

[11] Patent Number: 4,780,841

[45] Date of Patent: Oct. 25, 1988

[54] METHOD AND APPARATUS FOR STABILIZING MEASURED VALUES FOR DISPLAY

[75] Inventors: Singo Ichikawa; Yasuo Kamiyama, both of Sayama, Japan

[73] Assignee: Citizen Watch Co., Tokyo, Japan

[21] Appl. No.: 788,986

[22] Filed: Oct. 18, 1985

[30] Foreign Application Priority Data

Oct. 31, 1984 [JP] Japan .................. 59-229393

[51] Int. Cl.$^4$ .................................. G06F 15/36
[52] U.S. Cl. ....................................... 364/734
[58] Field of Search ............ 364/734, 575, 811, 812; 177/25, 25.14

[56] References Cited

U.S. PATENT DOCUMENTS

| | | | |
|---|---|---|---|
| 4,303,979 | 12/1981 | Kato et al. | 364/485 |
| 4,347,903 | 9/1982 | Yano et al. | 177/25 |
| 4,553,619 | 11/1985 | Fujinaga | 177/185 |
| 4,660,160 | 4/1987 | Tajima et al. | 364/567 |

Primary Examiner—Gary V. Harkcom
Assistant Examiner—Tan V. Mai
Attorney, Agent, or Firm—Townsend and Townsend

[57] ABSTRACT

A method and apparatus processes data representing measured values which are liable to show a poor consistency. Measured values are formed in groups; an average value and a discreteness value of a first group of measured values are calculated; an average value is presented as a most appropriate value to a display only when the discreteness value is below a reference value; otherwise, an average value and a discreteness value of the first and additional groups of measured values are calculated, and the recalculation is continued until the discreteness value has come to be below a reference value which decreases with the number of additional groups of measured values of which an average value and a discreteness value are calculated. The average value is presented as a most appropriate value to a display when the discreteness value is below the reference value.

9 Claims, 2 Drawing Sheets

METHOD AND APPARATUS FOR STABILIZING MEASURED VALUES FOR DISPLAY

BACKGROUND OF THE INVENTION

Field of the Invention

The present invention relates to a method and apparatus for processing data which varies with time, for instance, pulse rates, and more particularly to a method and apparatus for stabilizing measured values for the purpose of display.

During recent years, an increasing number of people have been engaging in regular exercise in order to keep fit. It is said that exercise appropriate for the purpose of keeping fit is hard enough to keep pulse rates ranging from 70 to 80 percent of maximum pulse rates. In an attempt to meet a desire for measuring pulse rates during exercise, wrist watches equipped with pulse rate monitors have been produced and been commercially available. There are two different kinds of pulse rate monitors: that is, one using a photoelectric type detector and the other using an electrocardiograph type detector. In the former type detector pulse rates are determined electro-optically in terms of blood flow rates in a finger with the finger put on a photoelectric sensor, which is fixed to the casing of a wrist-watch. In the latter type detector pulse rates are determined in terms of electric potential appearing on a finger with the finger put on a cardiograph sensor, which is fixed to the casing of a wrist-watch, too. Also, there are two different methods of determining pulse rates on the basis of the signals supplied by the cardiograph sensor. One method might be called "direct measuring method", in which the number of pulse detection signals per minute is counted and the count is displayed as an instantaneous pulse rate (see Japanese Patent Application Laid-Open No. 59-91389). The other method might be called "interpulse period equivalent measuring method", in which the interpulse periods of two to ten pulse detection signals are measured, and then a pulse rate per minute is estimated on the basis of the interpulse periods thus determined.

In these conventional pulse rate measuring methods, however, there are problems which make conventional pulse rate meters difficult to handle.

Specifically, the "direct measuring method" takes as long as one minute to complete a single measurement. In this connection, the value of the pulse rate when displayed, is stable, but it takes too much time to permit the continuous measurement of pulse rate. In contrast, the "interpulse period equivalent measuring method" is essentially a sampling measurement conducted at regular intervals of two to ten pulses. Therefore, it requires as short a measurement time as would permit the continuous measurement of pulse rate. However, as usually observed in the sampling measurement, disadvntageously the sampled and measured value varies at each and every measurement, and therefore the result of measurement is hardly reliable because of their inconsistency.

SUMMARY OF THE INVENTION

One object of the present invention is to provide an interpulse period equivalent measuring method, guaranteed free of the above mentioned drawback, stabilizing the values of all the measurements for the purpose of display, and still retaining the advantage of as short a measurement time as could permit the continuous measurement.

Another object of the present invention is to provide an apparatus for stabilizing measured values which show poor consistency.

To attain these objects a data processing method according to the present invention includes the steps of calculating an average value and a discreteness value of a group of measured values; comparing the discreteness value thus calculated with a given reference value; displaying the average value in case that the discreteness value is below the reference value; otherwise, recalculating an average value and a discreteness value of additional group or groups of measured values until the discreteness value is below a reference value, which decreases with the increase of the number of additional groups; and displaying the average value when the discreteness value is below the reference value. A data processing apparatus according to the present invention includes a data memory having a plurality of memory sections, an input for permitting entrance of measured data to a selected memory section, and an output for permitting access to selected memory sections. An average calculating circuit is connected to the output and creates an average value from one or more groups of measured values located in the data memory. A discreteness calculating circuit is connected to the output of the data memory and creates a discreteness value from one or more groups of memory values. A comparator is used to compare the discreteness value with a reference value created by a reference signal generator. The comparator provides a signal to a gate or display controlling circit only when the discreteness value is below the reference value. When this occurs the display controlling circuit permits the average value to be displayed at a display unit. When the discreteness value is not below the reference value for a particular group or groups of measured values (which indicates the values in the group or groups of measured values are not stable), then the average calculating unit and the discreteness calculating unit make their calculations using the particular group of measured values and an additional group of measured values from the memory unit. The reference value is decreased with the increase in number of groups of measured values used by the average calculating unit and the discreteness calculating unit to make their calculations.

BRIEF DESCRIPTION OF THE DRAWINGS

These and other objects and advantages of the present invention will be understood from the following description of a sole preferred embodiment of the present invention, which is shown in the accompanying drawings.

DETAILED DESCRIPTION OF A PREFERRED EMBODIMENT

Figure 1:
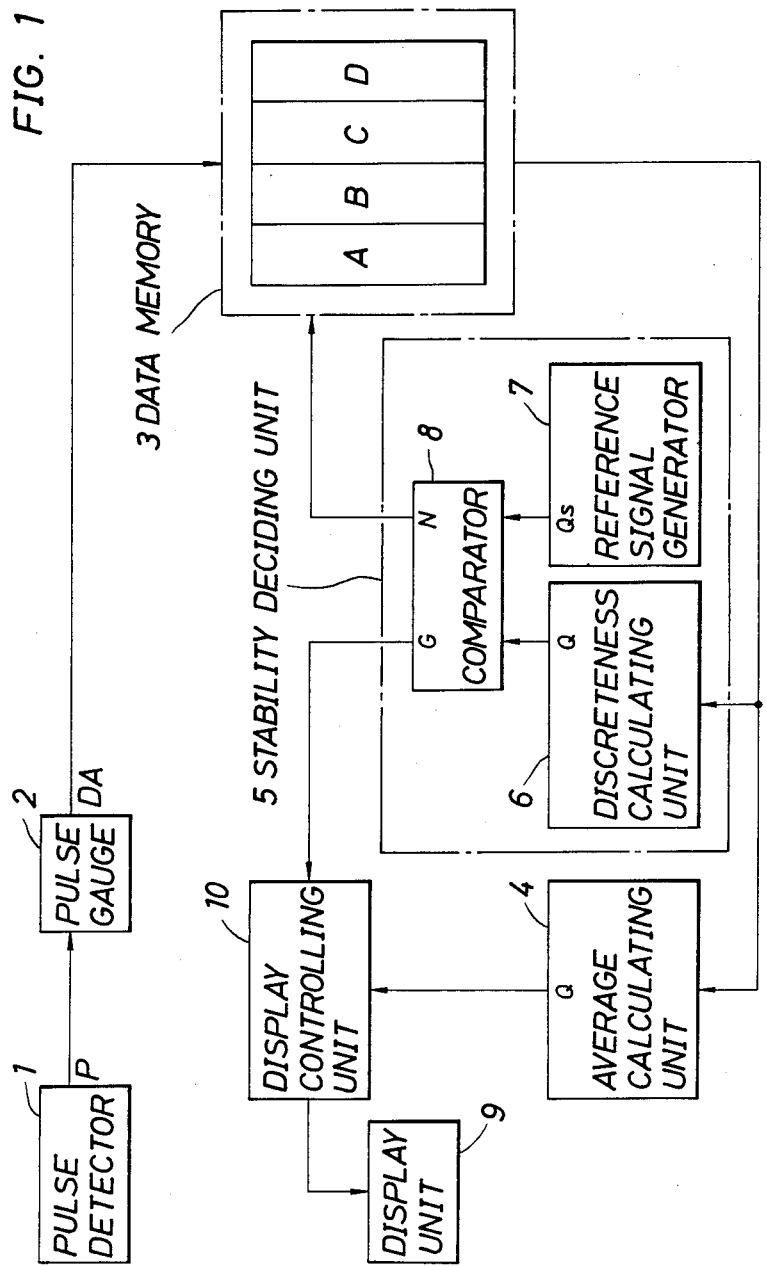
FIG. 1 is a block diagram showing a pulse rate meter according to one embodiment of the present invention.

FIG. 1 shows a data processing apparatus according to one embodiment of the present invention as being applied to a pulse rate meter. It comprises the following units: a pulse detector 1 responsive to pulse for providing a train of electric pulses P (hereinafter referred to as "sensor pulses"); a pulse gauge 2 responsive to the sensor pulses P for measuring interpulse period or interpulse length of time of the sensor pulses P and for providing an electric signal representing the number of user's pulses (hereinafter referred to as "measured data" DA); a data memory 3 for storing the measured data DA, composed of four memory sections A, B, C and D each capable of storing a plurality of data as constituting one group; an average calculating unit 4 for calculating the average of a group of data stored in each section of the data memory 3 and for providing an electric signal representing the calculated average value at the output terminal Q of the calculator; a stability deciding unit 5 for making a decision as to whether the measured data shows an inclination of great discreteness, said stability deciding unit 5 comprising discreteness calculating unit 6 for determining a standard deviation or any other value appropriate for representing the discreteness of the measured data of which an average is determined by the average calculating unit 4, a reference signal generator 7 for providing a reference signal as a standard for discreteness, and a comparator unit 8 for comparing the value of discreteness calculated by the discreteness calculating unit 6 with the reference signal from the reference signal generator 7 and for providing an electric signal at the output terminal G of the comparator when the value of discreteness is below the standard value and an electric signal at the output terminal N of the comparator when the value of discreteness is above the standard value; a display unit 9; and a display controlling unit 10 responsive to the appearance of an electric signal at the output terminal G of the comparator 8 for allowing the display unit 9 to show the data supplied by the average calculating unit 4 as the instantaneous pulse rate.

In operation a pulse sensor (not shown) associated with the pulse detector 1 is put on an appropriate part of a user's body, and then the pulse detector 1 supplies sensor pulses P to the pulse gauge 2. The pulse gauge 2 determines the interpulse period of subsequent or adjacent sensor pulses P, providing an electric signal representing measured data DA at the output terminal of the pulse gauge 2. The data memory 3 permits measured data DA to enter the memory section A until it is filled with the measured data DA. Thus, the first storage of measured data DA finishes, and then average and discreteness calculations follow.

The average calculating unit 4 calculates the average of the measured data stored in the memory section A to provide an electric signal representing the average of the measured data at the output terminal Q of the average calculator 4, and at the same time the discreteness calculating unit 6 calculates the standard deviation of the measured data stored in the memory section A to provide an electric signal representing the standard deviation at the output terminal Q of the discreteness calculating unit 6. Then, the comparator unit 8 compares the standard deviation with a given reference value. When the standard deviation is below the reference value, that is, when the pulse detector 1 detects pulses in so stable a situation as the interpulse periods remain at a substantially fixed value, an electric signal appears at the output terminal G of the comparator 8. The display controlling circuit 10 is responsive to the appearance of the electric signal at the output terminal G of the comparator 8 for allowing theoutput signal of the average calculating circuit 4 to pass to and appear in the display unit 9 as a stable pulse data representing the instantaneous pulse rate. So far as the detected pulses remain in a relatively stable condition, the storage of measured data in the memory section A, the calculations of the average and the standard dispersion and the display of pulse rate are repeated as described above, thus permitting the continuous measurement of pulse rates (each measurement of pulse rate advantageously being conducted in a possible minimum time).

It is, however, rare to be able to conduct a stable continuous measurement of pulse rates. The interpulse period is liable to be unstable for various reasons, for instance, unstable contact between the user's body and the sensor, or the adverse effect by exterior noises.

In case the interpulse periods remain unstable or irregular, the pulse rate meter operates as follows:

For the first measurement of pulse rates the average and standard deviation of the measured data stored in the memory section A are conducted as described above. The discreteness of the measured data DA, however, is so great that the standard deviation of the measured data calculated by the dispersion calculating circuit 6 is above the reference value, thus not permitting an electric signal to appear at the output terminal G of the comparator 8, and hence preventing the display of the pulse rate which is calculated by the average calculating circuit 4. Instead, an electric signal appears at the output terminal N of the comparator 8, thereby causing the data memory 3 to resume the storage of data, permitting measured data DA to enter the memory section B until it is filled with measured data. Then, the second data storage finishes, and the average and dispersion calculations of measured data start. In this second arithmetic operation, necessary calculations are conducted on the first group of measured data DA stored in the memory section A and the second group of measured data DA stored in the memory section B, as well. Thus, necessary calculations must be conducted on measured data twice as much as measured data in the earlier described occasion. Specifically, the average calculating circuit 4 and the dispersion calculating circuit 6 calculate the average and the standard deviation of the measured data stored in the memory sections A and B, respectively.

Then, the stability deciding unit 5 is brought into operation. The reference signal generator 7 is so constructed that the reference signal generated thereby decreases with the increase of the quantity of measured data at a fixed rate, and the comparator circuit 8 compares the standard deviation with a new reference value selected for two groups of measured data to provide an electric signal at either output terminal G or N of the comparator 8. As already described, the display controlling circuit 10 is responsive to the appearance of the electric signal at the output terminal G of the comparator 8 for allowing the display unit 9 to show the average value. However, in case the electric signal appears at the output terminal N of the comparator 8 again, the data memory 3 starts the third storage of measured data, allowing measured data DA to enter the memory section C to its full capacity. When the third storage of measured data finishes, the average and standard deviation of the measured data stored in the memory sections A, B and C (three times as much as the measured data in the first occasion) are calculated, and then the standard deviation is compared with a reduced reference value appearing at the output terminal of the reference signal generator 7. As a result of comparison either display or recalculation follows.

As may be understood from the above, in the case that the detected signal is so stable that the dispersion or discreteness of measured data remains at a reduced standard deviation, the first measurement presents the instantaneous pulse rate in a possible shortest time. In case the detected signal is so unstable that the discreteness of the measured data remains at an increased standard deviation, an increased number of measured data are subjected to the statistical treatment as described above, thereby stabilizing the value of pulse rate for display.

Figure 2:
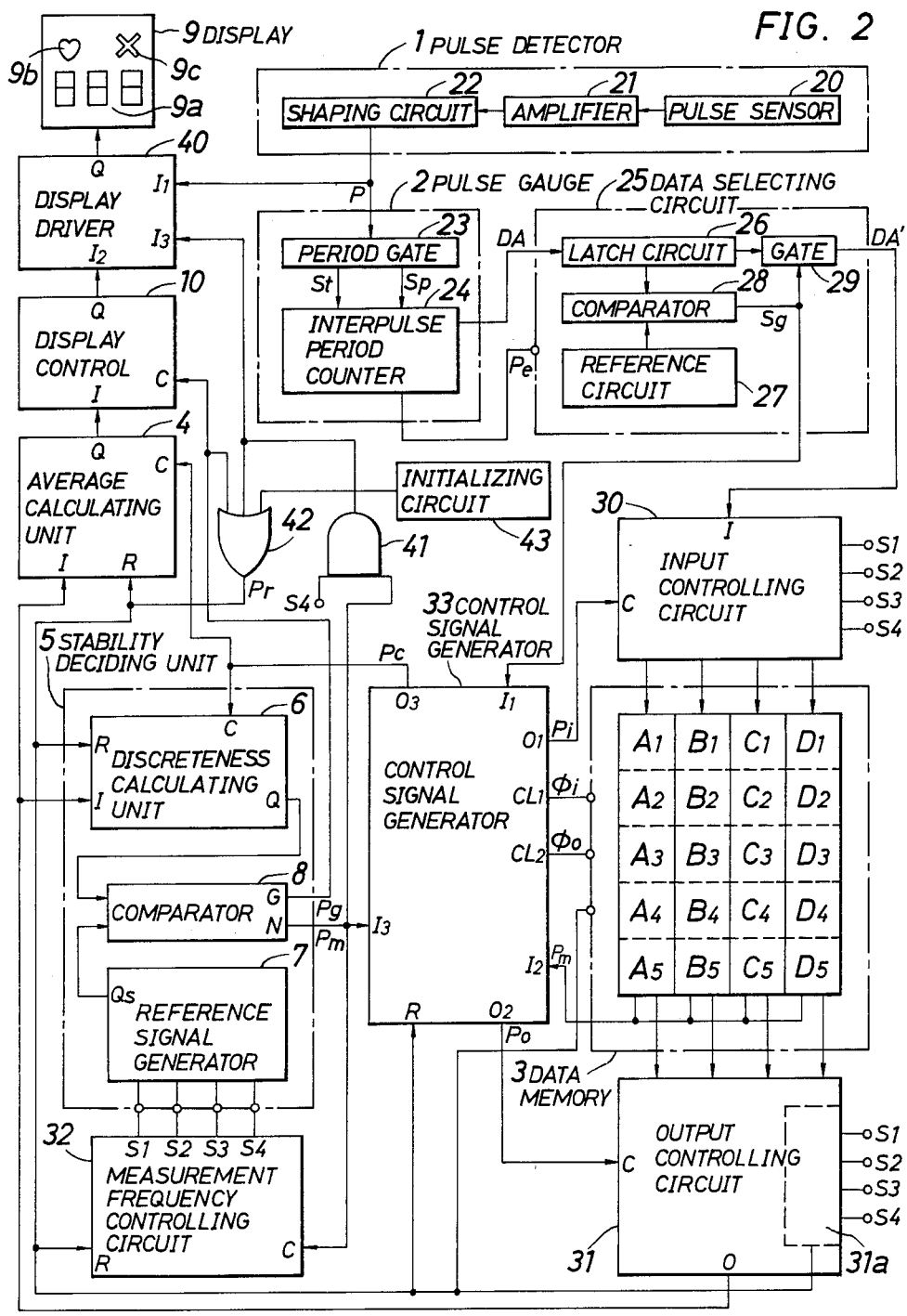
FIG. 2 is a block diagram showing the pulse rate meter of FIG. 1 in more detail.

FIG. 2 shows a pulse rate meter of FIG. 1 in more detail. The pulse detector 1 is shown as being composed of a pulse sensor 20 using a photocoupler (not shown), an amplifier circuit 21 for amplifying the pulse rate signal from the pulse sensor 20, and a shaping circuit 22 for shaping the pulse signal into sensor pulses P. The pulse gauge 2 is composed of a period gate circuit 23 for providing measurement starting signal ST and measurement ending signal SP for each sensor pulse P, and an interpulse period counter 24 for measuring interpulse periods under the control of the measurement starting and measurement ending signals ST and SP. The data selecting circuit 25 is composed of a latch circuit 26 for receiving measured data DA from the interpulse period counter 24, a reference circuit 27 for storing the upper and lower limit values of measured data DA as acceptable, a comparator circuit 28 for comparing the measured data DA held in the latch circuit with the upper limit value set in the reference circuit 27, and a gate circuit 29 for opening and closing in response to gate signal Sg which appears at the output terminal of the comparator 28 in case that measured data DA is within the range defined by the upper and lower limits stored in the reference circuit 27. The data selecting circuit is brought into operation when the interpulse period counter 24 supplies measurement ending pulse Pe.

Specifically, the latch circuit 26 responds to the appearance of pulse Pe for latching the measured data DA, and at the same time, the comparator 28 compares the so latched data with the upper and lower limit values set in the reference circuit 27. When the measured data DA is found to be within the range between the upper an lower limit values, the gate signal Sg appears at the output terminal of the comparator 28, and then the gate circuit 29 opens, thereby releasing the measured data DA from the latch circuit 26. The values which cannot be those of normal pulse rates are selected and set for the upper and lower limit values (for instance, 200 and 30). Thus, the data selecting circuit 25 is effective to eliminate wrong measured data and exterior noises, allowing only normal measured data to pass to the data memory 3.

As shown in FIG. 2, the data memory 3 comprises four memory sections A, B, C and D, each including five memory cells $A_1$ to $A_5$, $B_1$ to $B_5$, $C_1$ to $C_5$, and $D_1$ to $D_5$. When each memory section is filled with measured data, a storage ending pulse Pm appears at the output terminal of the final memory cell $A_5$, $B_5$, $C_5$ or $D_5$ of each memory section. An input controlling circuit 30 and an output controlling circuit 31 are connected to the data memory 3. The input and output controlling circuits 30 and 31 are responsive to designation signals applied to designation terminals $S_1$ to $S_4$ from a measurement frequency controlling circuit 32 (later described) and different control signals from a control signal generator circuit 33 for permitting entrance of measured data to the memory unit 3 and for permitting release of measured data from the memory unit 3. As shown, the output controlling circuit 31 includes a designation memory 31a.

The measurement frequency controlling circuit 32, for setting the number of times that measurements are made, has a clock terminal C, a reset terminal R and four designation terminals $S_1$, $S_2$, $S_3$ and $S_4$. When an input signal is applied to the clock terminal C of the control 32, the four designation terminals $S_1$ to $S_4$ are selected or designated cyclically, and when an input signal is applied to the reset terminal R of the control 32 the situation returns to the one in which the designation terminal $S_1$ is selected or designated. The data dispersion calculating circuit 6 in the stability deciding unit 5 is responsive to application of an arithmetic operation command signal to the control terminal C of the calculator 6 for calculating a standard deviation S of the measured data supplied to the input terminal 1 of the calculator, thus providing an electric signal representing the standard deviation at the output terminal Q of the calculator 6.

The value of the reference signal generated by the reference signal generator 7 and appearing at the output terminal Qs thereof reduces at a fixed ratio as designation signals $S_1$ to $S_4$ from the measurement frequency controlling circuit 32 are applied to the reference signal generator one after another. The comparator circuit 8 compares the standard deviation S from the data dispersion calculating circuit 6 with the reference signal R from the reference signal generator 7. The comparator 8 provides a pulse signal Pg at the output terminal G of the comparator or otherwise, a pulse signal Pn at the output terminal N of the comparator, depending on the result of comparison.

The average calculating unit 4 is responsive to application of the arithmetic operation command signal to the control terminal C of the calculator 4 for reading the measured data supplied to the input terminal I of the calculator and calculating the average of the measured data, providing an electric signal representing the average value at the output terminal Q of the calculator. As shown, the display unit 9 includes a pulse rate display 9a for showing a three-digit display, a heart indicating "able to measure" and a cross 9c indicating "unable to measure".

The display controlling circuit 10 is responsive to application of a latch signal Pg from the comparator 8 to the control terminal C of the display control 10 for storing the pulse rate average supplied to the input terminal I of the display control, providing the pulse rate average in the condition of being available to the display unit 9 at the output terminal Q of the display control 10. A display driver circuit 40 is responsive to application of different signals to the input terminals $I_1$, $I_2$ and $I_3$ of the driver 40 for providing different signals at the output terminal Q of the driver, thus driving selected display or indications 9a, 9b or 9c in the display unit 9. Specifically when a sensor pulse P is applied to the input terminal $I_1$ of the display driving circuit 40, the heart 9b goes on and off, thereby indicating that a user's pulse is being measured. At the same time, the pulse rate average which is supplied to the display driving circuit 40 by the display control 10, is shown in a three-digit number in the pulse rate display 9a. When a signal is applied to the input terminal $I_3$ of the display driver 40, the cross mark 9c turns on, indicating "unable to measure". An initializing circuit 43 is responsive to the "throw-in" of a power supply for generating a reset signal.

The operation of the pulse rate meter of FIG. 2 is described below with reference to the operation of the control signal generator circuit 33.

At first, a power supply is thrown in the pulse rate meter by turning an associated switch (not shown) on, and then an electric signal is generated by the initializing circuit 43, and is applied via an OR gate 42 to the average calculating circuit 4, the discreteness calculating circuit 6, the measurement frequency controlling circuit 32, the control signal generator circuit 33 and the data memory 3 as a reset pulse Pr, thus resetting these units. As a result the average calculating circuit 4 and the discreteness calculating circuit 6 are brought into their stand-by situations; the measurement frequency controlling circuit 32 is reset to the state of selecting $S_1$; the data memory 3 is cleared away; and finally the control signal generator 33 is brought in the situation in which: a control signal Pi appears at the output terminal $O_1$ of the control signal generator 33, thereby putting the input controlling circuit 30 into operation; and clock signals $\phi i$ and $\phi o$ are ready to appear at the output terminal $CL_1$ and $CL_2$ of the control signal generator 33. Then, a user puts his finger on the pulse sensor 20, thereby providing a train of pulses. They are amplified in the amplifier 21, and are shaped to sensor pulses P by the shaping circuit 22. The sensor pulses P are directed both to the pulse rate gauge 2 and to the display driving circuit 40. Then, the display driver 40 permits the display unit 9 to turn its heat mark 9b on and off at the period of sensor pulses P, thereby indicating that the user's pulse is being measured.

The period gate circuit 23 responds to the sensor pulses P for providing start and stop signals St and Sp alternately at the output terminals of the gate 23, and the interpulse period counter 24 provides measured data DA and a measurement ending pulse Pe at the end of each measurement. The measured data and the measurement ending pulse Pe are directed to the data selecting circuit 25.

The latch circuit 26 responds to the measurement ending signal Pe to hold the measured data DA. The comparator circuit 28 compares the measured data thus latched with the upper and lower limit values set in the reference circuit 27. If the measured data DA remains in the range defined by the upper and lower limits, the comparator 28 provides a gate signal Sg to open the gate 29. Also, the gate signal Sg is directed to the input terminal $I_1$ of the control signal generator circuit 33. As a result the control signal generator 33 provides a train of writing clock pulses; at the output terminal $CL_1$ of the generator 33, and these clock pulses, are directed to the data memory 3. The input controlling circuit 30 has been already brought into operation in response to the input controlling signal P1. An electric signal is applied to the input terminal $S_1$ of the input controlling circuit 30, thereby putting the input controlling circuit 30 in the writing mode with respect to the memory section A of the data memory 3. Thus, first the measured data DA' after passing through the gate 29 enters the memory cell $A_1$ under the control of the wiring clock pulses $\phi i$.

When the data selecting circuit 25 provides a subsequent gate signal Sg to the input terminal $I_1$ of the control signal generator 33, the signal $\phi i$ appears, thereby transferring the measured data from the memory cell $A_1$ to the memory cell $A_2$, and at the same time, a new measured data DA' is stored in the memory cell $A_1$. In this way, data transfer and storage are repeated until five measured data are stored in the memory cells $A_1$ to $A_5$. When the storage of the measured data in the memory cell $A_5$ is detected, a data-storing ending pulse Pm is generated and directed to the input terminal $I_2$ of the control signal generator circuit 33. As a result no input control signal Pi appears at the output terminal $O_1$ of the control signal generator 33; an output control signal Po appears at the output terminal $O_2$; and a train of reading clock pulses $\phi o$ appears at the output terminal $CL_2$. The output control signal Po and the clock pulses $\phi o$ are directed to the output controlling circuit 31 and to the data memory 3, respectively. With the terminal $S_1$ designated, the output controlling circuit 31 is brought to the access mode with respect to the memory section A of the data memory 3, thus transferring the measured data from the memory cells $A_1$ to $A_5$ to the average calculating circuit 4 and to the discreteness calculating unit 6 under the control of the reading clock pulses $\phi o$.

The control signal generator circuit 33 stops the output control signal Po simultaneously with the end of the reading clock pulses $\phi o$, and it provides the arithmetic operation command signal Pc at the output terminal $O_3$. In response to the arithmetic operation command signal the average calculating circuit 4 and discreteness calculating circuit 6 conduct calculations as required:

$$\text{average value } X = \frac{\sum\limits_{i=1}^{N} Xi}{N},$$

where $Xi$ stands for measured data ($i = 1, 2, \ldots N$), and $$\text{standard deviation } S_1 = \sqrt{\frac{\sum\limits_{i=1}^{N} (Xi - X)^2}{N}}$$

The discreteness calculating circuit 6 provides an electric signal representing a standard deviation $S_1$ at the output terminal Q of the calculator, and then the comparator circuit 8 compares the standard deviation with the first reference value $R_1$ supplied by the reference signal generator 7. As a result of comparison signal Pg or Pm appears at the output terminal G or N of the comparator, as described earlier.

The pulse rate meter functions as follows in case the standard deviation $S_1$ is smaller than the reference value $R_1$.

First, it should be noted that in case the discreteness value $S_1$ is smaller than the reference value $R_1$, measured data DA shows good consistency. Then, the signal Pg appears at the output terminal G of the comparator 8, thus causing the display control circuit 10 to hold the average value supplied by the average calculating circuit 4. Then, the so latched average value is supplied to the display unit 9 via the display control 40, and it appears in the pulse rate display 9a. At the same time the signal Pg passes through the OR gate 42, and it is applied as a reset pulse Pr to the average calculating circuit 4, the discreteness value calculating circuit 6, the measurement frequency control circuit 32, the designation memory 31a of the output controlling circuit 31, the control signal generator 33 and the data memory 3.

Thus, all of these circuits and units are reset, and the first measurement is finished. As the control signal generator 33 is reset, the input control signal Pi appears again, bringing the input controlling circuit 30 in operation to start the second measurement.

In case the standard deviation S is larger than the reference value $R_1$, the measured data DA shows a poor consistency. Then, the signal Pm appears at the output terminal N of the comparator 8. The signal Pm is applied to the input terminal $I_3$ of the control signal generator 33 and to the input terminal C of the measurement frequency controlling circuit 32, thereby switching designation terminals from $S_1$ to $S_2$. As a result the reference signal generator 7 provides a second reference signal at the second output terminal. The input controlling circuit 30 is brought into the mode of writing into the second memory section B as a result of designation of $S_1$. On the other hand, the output controlling circuit 31 is brought into the mode of continuous reading out from the memory sections A and B as a consequence of designation of $S_1$ and $S_2$ in the designation memory 31.

The control signal generator 33 responds to the signal Pm applied to its input terminal $I_3$ to provide a control signal Pi at its output terminal $O_1$, thus allowing measured data DA to pass through the input controlling circuit 30 and enter the memory section B. When the memory section B is filled with the measured data DA', a data storing ending signal Pm appears at the output terminal of the memory cell $B_5$. When the signal Pm is applied to the input terminal $I_2$ of the control signal generator 33, the control signal generator 33 brings output controlling circuit 3 to the access mode as described earlier.

In the second reading of measured data, however, the designation memory 31a designates the memory sections A and B, and therefore the measured data stored in the memory sections A and B, that is, ten groups of data are subjected to the average and discreteness calculations. Thus, an average value and a standard deviation $S_2$ of these ten groups of data result. Then, the standard deviation $S_2$ is compared with the second reference value $R_2$ provided by the reference signal generator 7. If the standard deviation $S_2$ is smaller than the second reference value, the average value is latched and displayed in the display unit.

If the standard deviation $S_2$ is still larger than the second reference value, and if a signal Pm appears at the output terminal of the comparator 8 again, the designation terminals of the measurement frequency controlling circuit 32 are switched from $S_2$ to $S_3$, thus putting the pulse rate meter in the stand-by condition for the third measurement, in which: measured data is directed to the memory section C; and fifteen groups of measured data are through the AND gate 41, which is ready to open with a signal applied to the terminal indicated at $S_4$. After passing through the AND gate the signal Pm is applied to the input terminal $I_3$ of the display driver circuit 40. Then, the cross mark 9c of the display unit 9 turns on, thereby indicating "unable to measure". At the same time, the signal Pm passes through the OR gate 42, and it functions as a reset pulse, resetting the units connected to the output terminal of the OR gate 42. As a result the pulse rate meter is brought to the intial condition, thus starting the first measurement.

The pulse rate meter performs the stabilization of the value to be displayed by repeating a series of operations as described earlier. As a matter of course the number of the times of repetition is not limted to four as in this particular embodiment, and as many times of repetition as required may be selected. Also, in this particular embodiment a standard deviation is used as an indication of inconsistency. This statistical value, however, should not be considered as limitative, and any other value appropriate for the purpose may be equally used. Programmed microcomputer systems may be used to constitute a pulse rate meter according to the above embodiment of the present invention. The present invention is described above as being applied to a pulse rate meter. This, however, should not be considered as limitative. The present invention may be equally applied to measurement of steps in walking, rotations per minute and any other function of time.

What we claim is:

1. A method for accurately measuring the pulse rate of a user under conditions in which the measured pulse rate is liable to show poor consistency comprising the steps of:

detecting the pulse of the user;

providing pulse signals in response to the detected pulse;

creating measured values according to the frequency of the pulse signals;

forming the measured values into a plurality of groups;

calculating an average value and a discreteness value of the first group of measured values;

comparing said discreteness value with a predetermined reference value;

presenting said average value as a most appropriate pulse rate value only when said discreteness value is below said reference value;

otherwise, recalculating another average value and another discreteness value using said first group of measured values and an additional group of measured values;

comparing said another discreteness value with the reference value;

presenting said another average value as a most appropriate pulse rate value only when said another discreteness value is below the reference value;

otherwise, repeating calculations of average and discreteness values utilizing further groups of measured values until the discreteness value is below the reference value; and presenting the average value as a most appropriate pulse rate value when the discreteness value is below the reference value.

2. A pulse rate measuring method according to claim 1 wherein a standard deviation is used as said discreteness value to show the degree of consistency of measured values.

3. A pulse rate measuring method according to claim 1 wherein each group contains the same number of measured values.

4. A pulse rate measuring method according to claim 1 wherein the reference value decreases, at a fixed rate, with the increase of the number of additional groups of measured values for which an average value and a discreteness value are calculated.

5. A pulse rate measuring method according to claim 1 wherein it further comprises the step of selecting, among measured values, those which are within a predetermined range before grouping.

6. An apparatus for processing data representing measured values which are liable to show poor consistency comprising:

a data memory including a plurality of memory sections; inputting means for permitting entrance of measured data to a selected memory section; outputting means for permitting access to selected memory section or sections; an average calculating circuit connected to said outputting means; a discreteness calculating circuit connected to said outputting means; a comparator for comparing the discreteness value of a group or groups of measured values with a predetermined reference value; means for supplying the average value to a display when the discreteness value is below the reference value and otherwise not; means for permitting said average calculating circuit and said discreteness calculating circuit to access selected group or groups of measured values stored in said data memory and for making said average and discreteness calculating circuits perform their respective calculations when the discreteness value is above the reference value; and means for decreasing the reference value with the increase of the number of selected groups of measured values of which the average and discreteness calculations are to be performed.

7. An apparatus according to claim 6 wherein a standard deviation is used as said discreteness value to show the degree of consistency of the measured values.

8. An apparatus according to claim 6 wherein each group contains the same number of measured values.

9. An apparatus according to claim 6 wherein the decrease of the reference value is at a fixed rate.

* * * * *